(12) United States Patent
Almutairi et al.

(10) Patent No.: US 8,636,745 B2
(45) Date of Patent: Jan. 28, 2014

(54) ORTHOPEDIC SURGICAL PIN POSITIONING DEVICE

(76) Inventors: Mutlaq Almutairi, Mansouriya (KW); Hussain Almutairi, Mansouriya (KW)

(*) Notice: Subject to any disclaimer, the term of this patent is extended or adjusted under 35 U.S.C. 154(b) by 104 days.

(21) Appl. No.: 13/044,054

(22) Filed: Mar. 9, 2011

(65) Prior Publication Data
US 2012/0232560 A1 Sep. 13, 2012

(51) Int. Cl.
A61B 17/56 (2006.01)

(52) U.S. Cl.
USPC .............................. 606/96; 606/87; 606/104

(58) Field of Classification Search
USPC ......... 606/86 R, 87, 89, 96, 97, 104, 59, 105; 623/22.12
See application file for complete search history.

(56) References Cited

U.S. PATENT DOCUMENTS

| | | | |
|---|---|---|---|
| 4,037,592 A | 7/1977 | Kronner | |
| 4,271,832 A * | 6/1981 | Evans et al. | 606/59 |
| 4,541,424 A | 9/1985 | Grosse et al. | |
| 4,662,365 A * | 5/1987 | Gotzen et al. | 606/59 |
| 4,942,872 A * | 7/1990 | Jawish | 606/57 |
| 4,978,348 A * | 12/1990 | Ilizarov | 606/57 |
| 5,324,295 A | 6/1994 | Shapiro | |
| 5,649,930 A | 7/1997 | Kertzner | |
| 6,482,206 B2 * | 11/2002 | Schoenefeld | 606/59 |
| 6,656,189 B1 * | 12/2003 | Wilson et al. | 606/97 |
| 7,104,998 B2 | 9/2006 | Yoon et al. | |
| 7,201,756 B2 | 4/2007 | Ross et al. | |
| 7,241,298 B2 | 7/2007 | Nemec et al. | |
| 7,803,158 B2 * | 9/2010 | Hayden | 606/80 |
| 2009/0118733 A1 * | 5/2009 | Orsak et al. | 606/60 |

* cited by examiner

*Primary Examiner* — Todd Manahan
*Assistant Examiner* — Marcela I Shirsat
(74) *Attorney, Agent, or Firm* — Richard C. Litman

(57) ABSTRACT

An orthopedic drill guide and surgical pin positioning device includes a primary surgical pin for insertion into a fractured bone and a longitudinal drum supported on said primary surgical pin. A set screw is also provided in said longitudinal drum for preventing the longitudinal drum from rotation about the primary surgical pin. A transverse drum is also provided and is rotatably disposed in the longitudinal drum as is a set screw for fixing the position of the transverse drum with respect to the longitudinal drum. A secondary pin extends through the transverse drum and is fixed in a second position on the hard tissue of the fractured bone. Finally, a pair of aligned openings extends through the transverse drum for guiding a drill bit and locating a surgical pin within the broken bone.

3 Claims, 3 Drawing Sheets

ORTHOPEDIC SURGICAL PIN POSITIONING DEVICE

BACKGROUND FOR THE INVENTION

1. Field of the Invention

The present invention relates to an orthopedic surgical pin positioning device and more particularly to an orthopedic drill guide and surgical pin locating device.

2. Background of the Invention

Pin positioning devices and surgical procedures for positioning surgical pins are well known and have been in widespread public use for many years. For example, a guide pin locating tool and method is disclosed in a U.S. Pat. No. 4,037,592 of Kronner. As disclosed therein, a tool and method for use by a surgeon in the insertion of a hip nail guide pin within an upper end of a femur. The tool includes a base for temporary abutment against the femur which base is supported by an initial guide pin in place within the femur. A first guide member is positionably carried by the base and is indexed through 90 degrees for the taking of X-ray photographs within perpendicular planes. An optimum location for a second guide pin is plotted on the resulting X-ray photographs. The surgeon, in inserting the second guide pin, utilizes the first guide member and a second guide member if necessary, to provide a reference point outwardly spaced from the femur to aid him in seating the guide pin through a window in the femur wall into position within the femur neck and head. A method of inserting a second guide pin is also disclosed.

A more recent approach to an orthopedic centering tool is disclosed in a Kertzner U.S. Pat. No. 5,649,930. As disclosed therein a tool for guiding a surgical drill bit through the center of a target obstruction within a bone. An adjustable frame includes a pair of right angle sections mounted in a mirror image relationship. The sections are adjustably clamped to one another and in turn, secure a vertical sleeve for guiding a surgical drill bit and a horizontal sleeve for accommodating an anchor pin within a coplanar arrangement. Various clamps associated with the frame elements and the sleeves permit a surgeon to adjust the tool so that the drill bit is guided through the vertical sleeve to the approximate center of the bone immediately below the obstruction while the pin anchors the frame to the bone.

A still further approach to orthopedic tools is disclosed in a U.S. Pat. No. 7,201,756 of Ross et al. The Ross et al. patent discloses surgical assist device and method that can be used to assist a surgeon in site selection and suture placement to re-attach the glenoid labrum to the shoulder's glenoid bone. The device and method includes an arcuate shaped bow arm, an angle guide attached to the bow arm at a selected location along the bow arm, a sleeve guide, and a target tool releaseably connected to the angle guide. A tip end of the sleeve guide is extended in surgery and is configured to intersect and pass through an aperture of the target tool. The tip end of the sleeve guide includes at least one tooth that embeds in the glenoid bone and holds the sleeve guide in position. A guide pin such as a suture carrier is extended through the sleeve guide. The sleeve guide is then removed leaving the sutures in the correct repair location.

Notwithstanding the above, it is presently believed that there is a need and a potential commercial market for an orthopedic drill guide and surgical pin positioning device in accordance with the present invention. There should be a need and commercial market for such devices because they provide accurate positioning of surgical pins and reduce the duration of time for surgical procedures involved in the placement of surgical pins by 40 to 60%. Further, the devices in accordance with the present invention are durable, easy to use and optimize the positioning of surgical pins.

BRIEF SUMMARY OF THE INVENTION

In essence an orthopedic drill guide and pin positioning device in accordance with a preferred embodiment of the invention includes a primary surgical pin for insertion into the hard tissue of a fractured bone and a longitudinal drum that is supported on the primary surgical pin. Means are also provided for preventing the longitudinal drum from rotation about the primary surgical pin. Further, a transverse drum is rotatably disposed in the longitudinal drum together with means for fixing the position of the transverse drum with respect to the longitudinal drum. A secondary pin extends through the transverse drum and is fixed into a second position of the hard tissue of the fractured bone. In addition, means such as a pair of aligned small openings extend through the transverse drum and serve as guides for a drill and for locating a surgical pin in the broken bone. Finally, an angle iron is provided for measuring the clockwise or counter-clockwise rotation of the transverse drum.

The invention will now be described in connection with the following drawings.

DESCRIPTION OF THE PREFERRED EMBODIMENTS OF THE INVENTION

Figure 1:
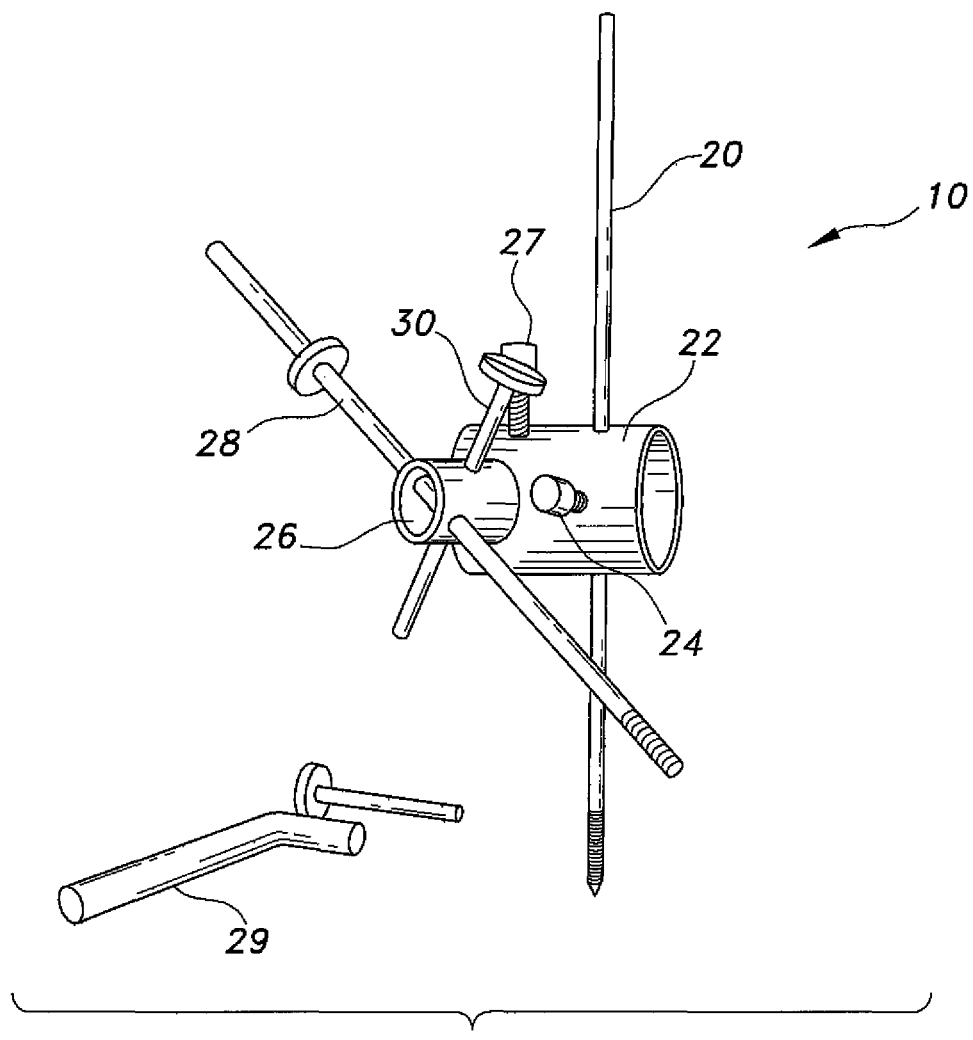
FIG. 1 is a perspective view of an orthopedic drill guide and surgical pin positioning device in accordance with a preferred embodiment of the invention.

As illustrated in FIG. 1 an orthopedic drill guide and surgical pin positioning device 10 in accordance with a preferred embodiment of the invention includes a primary surgical pin 20 for insertion into the hard tissue of a fractured bone and a longitudinal drum 22 supported on the primary surgical pin. The drum 22 has a length of about 1 inch (2.54 cms) and a diameter of about ¾ inch (1.91 cms). A set screw 24 or the like is provided to prevent the longitudinal drum from rotating about the surgical pin 20.

A transverse drum 26 having a diameter of about ¼ inch (0.64 cms) is rotatably disposed on one side of the longitudinal drum 22 near a rear portion thereof and includes a first pair of aligned openings for a secondary pin 28. The pin 28 is anchored in another portion of the fractured bone. The transverse drum 26 also includes a second pair of aligned openings and a third surgical pin 30 extending through the second pair of aligned openings and a 90° displacement with respect to the secondary pin 28. The transverse drum 26 as well as the surgical pin 30 like the longitudinal drum 22 and primary surgical pin 20 are also made of stainless steel. The transverse drum 26 is fixed in place by a vertically disposed screw 27 but is rotatable clockwise or counterclockwise to position a drill or pin under X-ray guidance. An angle iron 29 is used to measure the angle with respect to the primary pin 20.

The second pair of openings is used as a drill guide for guiding a drill for positioning a third surgical pin 30 in the fractured bone.

Figure 2:
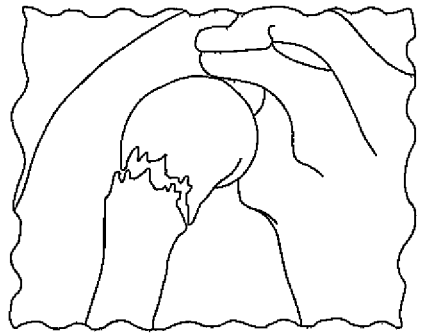
FIG. 2 is a schematic illustration of a displaced shoulder fracture.
Figure 3:
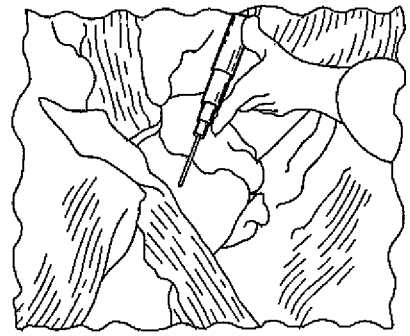
FIG. 3 is a schematic illustration of a primary pin being inserted proximal to a deltoid.
Figure 4:
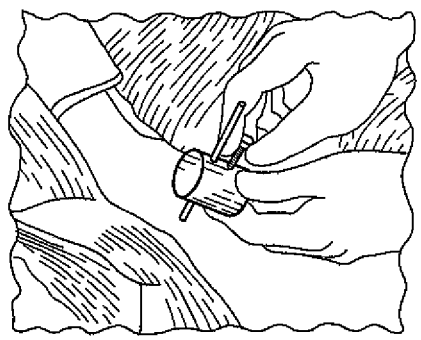
FIG. 4 illustrates a longitudinal drum being attached to the primary pin.
Figure 5:
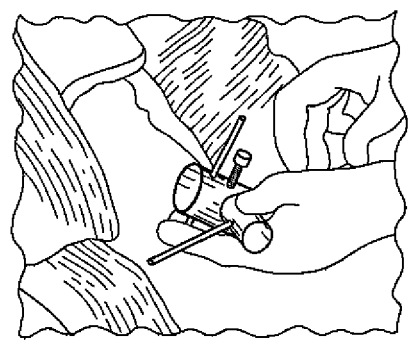
FIG. 5 illustrates a transverse drum being rotated and directed under X-ray guidance.
Figure 6:
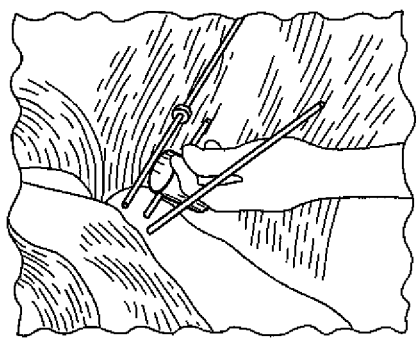
FIG. 6 illustrates multiple pins being inserted under X-ray guidance.
Figure 7:
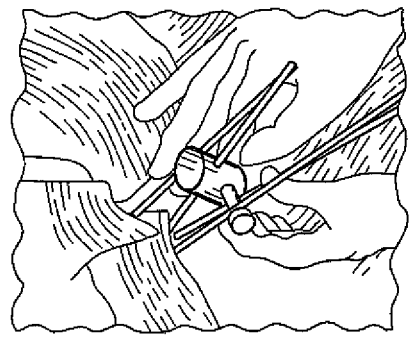
FIG. 7 illustrates the insertion of the pins into drilled holes in a fractured bone.

An example of the use of an orthopedic drill guide and surgical pin positioning device 10 in accordance with a preferred embodiment of the invention will now be described in connection with FIGS. 2-7. As illustrated in FIG. 2, a displaced shoulder fracture is prepared for repair and a primary pin is inserted after drilling a hole into the head and neck portion proximal to a deltoid insertion as illustrated in FIG. 3. As shown in FIG. 4, the longitudinal drum is attached to the primary pin and in FIG. 5 the transverse drum is positioned and fixed in place for positioning a secondary pin under X-ray guidance. FIG. 6 illustrates the insertion of multiple pins under X-ray guidance while FIG. 7 illustrates the positioning of multiple pins.

Figure 8:
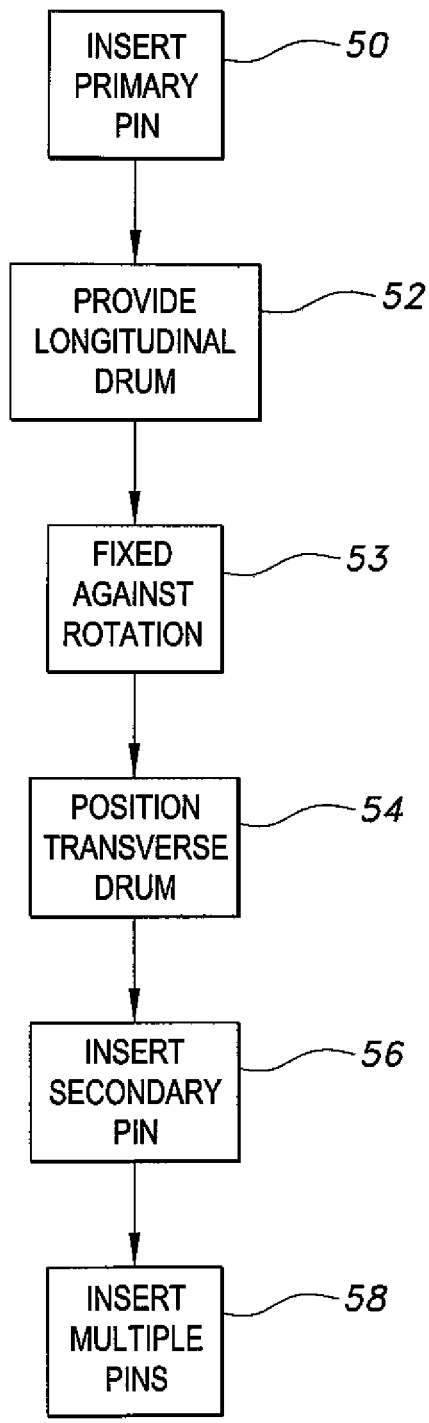
FIG. 8 is a block diagram illustrating a preferred method for surgical pin placement in accordance with the present invention.

A method for positioning surgical pins in the head and neck portion of a broken femur will now be described in connection with FIG. 8. As illustrated in FIG. 8, the method in accordance with a preferred embodiment of the invention includes a first step 50 of inserting a primary surgical pin in the neck and head portion of a broken femur. In the second step 52 a longitudinal drum is provided and supported on the primary pin and fixed against rotation in step 53 thereon as for example by turning a set screw that engages the primary pin. A next step 54 as illustrated in FIG. 8 includes positioning a transverse drum by rotating the transverse drum under X-ray guidance to position a secondary pin in step 56. Then in a fourth step 58 illustrated in FIG. 8, multiple pins are positioned under X-ray guidance and inserted as shown.

While the invention has been described in connection with its preferred embodiments it should be recognized that changes and modifications may be made therein without departing from the scope of the appended claims.

What is claimed is:

1. An orthopedic drill guide and surgical pin positioning device consisting of:
   a primary surgical pin for insertion into the hard tissue of a fractured bone and a longitudinal hollow drum supported on the primary pin and means for preventing the longitudinal drum from rotation about the primary surgical pin, wherein the longitudinal hollow drum has a first and second end and an outer surface;
   a transverse hollow drum rotatably disposed in the longitudinal drum through the outer surface thereof and being located adjacent the first end of the longitudinal drum, the transverse hollow drum having an outer surface including a first and second pair of aligned openings therethrough, wherein each of the pair of openings are fixedly, axially displaced;
   means for fixing the position of the transverse drum with respect to the longitudinal drum, wherein the means for fixing the position of the transverse drum extends through the outer surface of the longitudinal drum;
   a secondary surgical pin extending through the first pair of openings of the transverse drum along an axis spaced from the longitudinal drum and adapted to be fixed into a second position of hard tissue of the fractured bone; and
   a third surgical pin extending through the second pair of openings of the transverse drum along a 90 degree displacement from the secondary pin and adapted to be fixed into a third position of hard tissue of the fractured bone.

2. An orthopedic drill guide and surgical pin positioning device according to claim 1 in which said means for fixing the position of said transverse drum is a screw.

3. An orthopedic drill guide and surgical pin positioning device according to claim 2 in which said pins, drums and screws are made of stainless steel.

\* \* \* \* \*